(12) United States Patent
Hahn et al.

(10) Patent No.: US 11,497,914 B2
(45) Date of Patent: Nov. 15, 2022

(54) SYSTEMS AND METHODS FOR MAKING AND USING AN ELECTRICAL STIMULATION SYSTEM WITH A CASE-NEUTRAL BATTERY

(71) Applicant: Boston Scientific Neuromodulation Corporation, Valencia, CA (US)

(72) Inventors: Benjamin Phillip Hahn, Stevenson Ranch, CA (US); David M. Dorman, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 499 days.

(21) Appl. No.: 16/247,447

(22) Filed: Jan. 14, 2019

(65) Prior Publication Data
US 2019/0217102 A1     Jul. 18, 2019

Related U.S. Application Data

(60) Provisional application No. 62/617,992, filed on Jan. 16, 2018.

(51) Int. Cl.
*A61N 1/372* (2006.01)
*A61N 1/36* (2006.01)
(Continued)

(52) U.S. Cl.
CPC .......... *A61N 1/36135* (2013.01); *A61N 1/36* (2013.01); *A61N 1/36128* (2013.01);
(Continued)

(58) Field of Classification Search
CPC ........ A61N 1/378; A61N 1/36; A61N 1/0534; A61N 1/36135; A61N 1/36139; A61N 1/36142
See application file for complete search history.

(56) References Cited

U.S. PATENT DOCUMENTS

| 979,652 A | 12/1910 | Church |
| 2,186,277 A | 1/1940 | Tetens |

(Continued)

FOREIGN PATENT DOCUMENTS

| EP | 0911061 | 4/1999 |
| JP | S55-112538 | 7/1980 |

(Continued)

OTHER PUBLICATIONS

International Search Report and Written Opinion for PCT Application No. PCT/US2019/013531 dated Apr. 1, 2019.

(Continued)

*Primary Examiner* — Michael J D'Abreu
(74) *Attorney, Agent, or Firm* — Branch Partners PLLC; Bruce E. Black

(57) ABSTRACT

A control module for an electrical stimulation system includes a sealed electronics housing; an electronic subassembly disposed within the electronics housing; one or more connector assemblies coupled to the electronic subassembly; and a rechargeable battery disposed external to the electronics housing. The one or more connector assemblies are configured to receive a lead. The rechargeable battery includes a positive electrode, a negative electrode, and a single battery case attached directly to the sealed electronics housing and forming a sealed cavity that encapsulates both the positive electrode and the negative electrode. The battery case is electrically isolated from each of the positive electrode and the battery electrode.

16 Claims, 7 Drawing Sheets

(51) Int. Cl.
*A61N 1/378* (2006.01)
*A61N 1/375* (2006.01)
*A61N 1/05* (2006.01)
*A61B 17/34* (2006.01)

(52) U.S. Cl.
CPC ..... *A61N 1/36139* (2013.01); *A61N 1/36142* (2013.01); *A61N 1/378* (2013.01); *A61N 1/3754* (2013.01); *A61B 17/3468* (2013.01); *A61N 1/0534* (2013.01); *A61N 1/3605* (2013.01); *A61N 1/3752* (2013.01); *A61N 1/37514* (2017.08); *A61N 1/37518* (2017.08)

(56) References Cited

U.S. PATENT DOCUMENTS

| | | |
|---|---|---|
| 2,521,301 A | 9/1950 | Morrison |
| 2,873,822 A | 2/1959 | Sloan |
| 2,912,712 A | 11/1959 | Shamban et al. |
| 3,758,827 A | 9/1973 | Schroder et al. |
| 3,826,952 A | 7/1974 | Iwasaki et al. |
| 3,829,737 A | 8/1974 | Johnsson |
| 4,114,603 A | 9/1978 | Wilkinson |
| 4,245,645 A | 1/1981 | Arseneault et al. |
| 4,297,609 A | 10/1981 | Hirao et al. |
| 4,315,180 A | 2/1982 | Kondo et al. |
| 4,328,313 A | 5/1982 | Simonson et al. |
| 4,328,313 A | 5/1982 | Ray |
| 4,467,800 A | 8/1984 | Zytkovicz |
| 4,741,571 A | 5/1988 | Godette |
| 4,805,634 A | 2/1989 | Ullrich et al. |
| 4,826,487 A | 5/1989 | Winter |
| 4,850,359 A | 7/1989 | Putz |
| 4,931,056 A | 6/1990 | Ghajar et al. |
| 4,955,891 A | 9/1990 | Carol |
| 4,998,938 A | 3/1991 | Ghajar et al. |
| 5,116,345 A | 5/1992 | Jewell et al. |
| 5,193,539 A | 3/1993 | Schulman et al. |
| 5,193,540 A | 3/1993 | Schulman et al. |
| 5,201,737 A | 4/1993 | Leibinger et al. |
| 5,235,990 A | 8/1993 | Dempsey |
| 5,300,080 A | 4/1994 | Clayman et al. |
| 5,324,316 A | 6/1994 | Schulman et al. |
| 5,330,485 A | 7/1994 | Clayman et al. |
| 5,464,446 A | 11/1995 | Dreessen et al. |
| 5,484,445 A | 1/1996 | Knuth |
| 5,496,356 A | 3/1996 | Hudz |
| 5,503,164 A | 4/1996 | Friedman |
| 5,549,620 A | 8/1996 | Bremer |
| 5,707,373 A | 1/1998 | Sevrain et al. |
| 5,732,699 A | 3/1998 | Lundback |
| 5,776,144 A | 7/1998 | Levsieffer et al. |
| 5,800,504 A | 9/1998 | Bellifemine |
| 5,843,150 A | 12/1998 | Dreessen et al. |
| 5,865,842 A | 2/1999 | Knuth et al. |
| 5,891,028 A | 4/1999 | Lundback |
| 5,897,531 A | 4/1999 | Amirana |
| 5,916,154 A | 6/1999 | Hobbs et al. |
| 5,927,277 A | 7/1999 | Baudino et al. |
| 5,954,687 A | 9/1999 | Baudino |
| 5,984,930 A | 11/1999 | Maciunas et al. |
| 5,993,463 A | 11/1999 | Truwit |
| 6,006,124 A | 12/1999 | Fischell et al. |
| 6,016,449 A | 1/2000 | Fischell et al. |
| 6,044,304 A | 3/2000 | Baudino |
| 6,050,098 A | 4/2000 | Meyer et al. |
| 6,050,998 A | 4/2000 | Fletcher |
| 6,073,048 A | 6/2000 | Kieval et al. |
| 6,094,598 A | 7/2000 | Elsberry et al. |
| 6,117,143 A | 9/2000 | Hynes et al. |
| 6,126,663 A | 10/2000 | Hair |
| 6,128,537 A | 10/2000 | Rise |
| 6,128,538 A | 10/2000 | Fischell et al. |
| 6,134,474 A | 10/2000 | Fischell et al. |
| 6,134,477 A | 10/2000 | Knuteson |
| 6,171,239 B1 | 1/2001 | Humphrey |
| 6,175,710 B1 | 1/2001 | Kamaji et al. |
| 6,181,969 B1 | 1/2001 | Gord |
| 6,200,329 B1 | 3/2001 | Fung et al. |
| 6,210,417 B1 | 4/2001 | Baudino et al. |
| 6,224,450 B1 | 5/2001 | Norton |
| 6,230,049 B1 | 5/2001 | Fischell et al. |
| 6,269,270 B1 | 7/2001 | Boveja |
| 6,271,094 B1 | 8/2001 | Boyd et al. |
| 6,284,729 B1 | 9/2001 | Bernfield et al. |
| 6,295,944 B1 | 10/2001 | Lovett |
| 6,321,104 B1 | 11/2001 | Gielen et al. |
| 6,324,433 B1 | 11/2001 | Errico |
| 6,353,762 B1 | 3/2002 | Baudino et al. |
| 6,354,299 B1 | 3/2002 | Fischell et al. |
| 6,356,729 B1 | 3/2002 | Sasaki et al. |
| 6,356,777 B1 | 3/2002 | Garfield et al. |
| 6,356,792 B1 | 3/2002 | Errico |
| 6,364,278 B1 | 4/2002 | Lin et al. |
| 6,374,140 B1 | 4/2002 | Rise |
| 6,391,985 B1 | 5/2002 | Goode et al. |
| 6,413,263 B1 | 7/2002 | Lobdill et al. |
| 6,427,086 B1 | 7/2002 | Fischell et al. |
| 6,447,443 B1 | 9/2002 | Keogh et al. |
| 6,459,936 B2 | 10/2002 | Fischell et al. |
| 6,463,328 B1 | 10/2002 | John |
| 6,464,687 B1 | 10/2002 | Ishikawa et al. |
| 6,466,822 B1 | 10/2002 | Pless |
| 6,480,743 B1 | 11/2002 | Kirkpatrick et al. |
| 6,482,182 B1 | 11/2002 | Carroll et al. |
| 6,516,227 B1 | 2/2003 | Meadows |
| 6,560,486 B1 | 5/2003 | Osorio et al. |
| 6,571,127 B1 | 5/2003 | Ben-Haim et al. |
| 6,574,498 B1 | 6/2003 | Gilboa |
| 6,597,954 B1 | 7/2003 | Pless et al. |
| 6,609,020 B2 | 8/2003 | Gill |
| 6,609,029 B1 | 8/2003 | Mann et al. |
| 6,609,032 B1 | 8/2003 | Woods et al. |
| 6,618,623 B1 | 9/2003 | Pless et al. |
| 6,647,296 B2 | 11/2003 | Fischell et al. |
| 6,690,974 B2 | 2/2004 | Archer et al. |
| 6,741,892 B1 | 5/2004 | Meadows et al. |
| 6,795,737 B2 | 9/2004 | Gielen et al. |
| 6,845,257 B2 | 1/2005 | Fuimaono et al. |
| 6,845,267 B2 | 1/2005 | Harrison et al. |
| 6,895,280 B2 | 5/2005 | Meadows et al. |
| 6,920,359 B2 | 7/2005 | Meadows et al. |
| 6,944,501 B1 | 9/2005 | Pless |
| 6,950,707 B2 | 9/2005 | Whitehurst |
| 7,004,948 B1 | 2/2006 | Pianca et al. |
| 7,033,326 B1 | 4/2006 | Pianca et al. |
| 7,050,855 B2 | 5/2006 | Zeijlemaker et al. |
| 7,090,661 B2 | 8/2006 | Morris et al. |
| 7,118,828 B2 | 10/2006 | Dodd et al. |
| 7,146,222 B2 | 12/2006 | Boling |
| 7,174,213 B2 | 2/2007 | Pless |
| 7,174,219 B2 | 2/2007 | Wahlstrand et al. |
| 7,177,701 B1 | 2/2007 | Pianca |
| 7,204,840 B2 | 4/2007 | Skakoon et al. |
| 7,212,864 B2 | 5/2007 | Wahlstrand et al. |
| 7,235,084 B2 | 6/2007 | Skakoon et al. |
| 7,242,982 B2 | 7/2007 | Singhal et al. |
| 7,244,150 B1 | 7/2007 | Brase et al. |
| 7,343,205 B1 | 3/2008 | Pianca et al. |
| 7,369,899 B2 | 5/2008 | Malinowski et al. |
| 7,421,297 B2 | 9/2008 | Gifakis et al. |
| 7,437,193 B2 | 10/2008 | Parramon et al. |
| 7,450,997 B1 | 11/2008 | Pianca et al. |
| 7,454,251 B2 | 11/2008 | Rezai et al. |
| 7,479,146 B2 | 1/2009 | Malinowski et al. |
| 7,548,775 B2 | 6/2009 | Kipke et al. |
| 7,636,596 B2 | 12/2009 | Solar |
| 7,672,734 B2 | 3/2010 | Anderson et al. |
| 7,682,745 B2 | 3/2010 | Howard et al. |
| 7,756,922 B2 | 7/2010 | Basu et al. |
| 7,761,165 B1 | 7/2010 | He et al. |
| 7,766,922 B1 | 8/2010 | Daglow et al. |
| 7,783,359 B2 | 8/2010 | Meadows |
| 7,787,945 B2 | 8/2010 | Greene |

(56) References Cited

U.S. PATENT DOCUMENTS

| | | |
|---|---|---|
| 7,792,590 B1 | 9/2010 | Pianca et al. |
| 7,809,446 B2 | 10/2010 | Meadows |
| 7,815,651 B2 | 10/2010 | Skakoon et al. |
| 7,833,231 B2 | 11/2010 | Skakoon et al. |
| 7,833,253 B2 | 11/2010 | Ralph et al. |
| 7,949,395 B2 | 5/2011 | Kuzma |
| 7,949,410 B2 | 5/2011 | Rodriguez |
| 7,974,706 B2 | 7/2011 | Moffitt et al. |
| 7,981,119 B2 | 7/2011 | Lando et al. |
| 8,024,045 B2 | 9/2011 | Carlton et al. |
| 8,043,304 B2 | 10/2011 | Barker |
| 8,137,362 B2 | 3/2012 | Malinowski |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,313,453 B2 | 11/2012 | Carbunaru et al. |
| 8,364,278 B2 | 1/2013 | Pianca et al. |
| 8,391,985 B2 | 3/2013 | McDonald |
| 8,397,732 B2 | 3/2013 | Singhal et al. |
| 8,425,534 B2 | 4/2013 | Barker |
| 8,473,061 B2 | 6/2013 | Moffitt et al. |
| 8,571,664 B2 | 10/2013 | Anderson et al. |
| 8,571,665 B2 | 10/2013 | Moffitt et al. |
| 8,688,235 B1 | 4/2014 | Pianca et al. |
| 8,731,686 B2 | 5/2014 | Lane et al. |
| 8,764,767 B2 | 7/2014 | Barker |
| 8,792,993 B2 | 7/2014 | Pianca et al. |
| 8,812,133 B2 | 8/2014 | Funderburk |
| 9,043,000 B2 | 5/2015 | Lane et al. |
| 9,050,191 B2 | 6/2015 | Funderburk |
| 9,084,901 B2 | 7/2015 | Wahlstrand |
| 9,101,756 B1 | 8/2015 | Pianca et al. |
| 9,468,751 B2 | 10/2016 | Bonde |
| 9,474,896 B2 | 10/2016 | Lopez |
| 9,492,660 B2 | 11/2016 | Mouchawar et al. |
| 9,604,052 B2 | 3/2017 | Behymer et al. |
| 9,610,437 B2 | 4/2017 | Okun et al. |
| 10,232,169 B2 | 3/2019 | Govea et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0052610 A1 | 5/2002 | Skakoon et al. |
| 2002/0072770 A1 | 6/2002 | Pless |
| 2002/0077670 A1 | 6/2002 | Archer et al. |
| 2002/0099412 A1 | 7/2002 | Fischell et al. |
| 2002/0156372 A1 | 10/2002 | Skakoon et al. |
| 2002/0169485 A1 | 11/2002 | Pless et al. |
| 2003/0028199 A1 | 2/2003 | Ghahremani et al. |
| 2003/0083724 A1 | 5/2003 | jog et al. |
| 2003/0088274 A1 | 5/2003 | Gliner et al. |
| 2003/0088303 A1 | 5/2003 | Goode |
| 2004/0034367 A1 | 2/2004 | Malinowski |
| 2004/0122446 A1 | 6/2004 | Solar |
| 2004/0153129 A1 | 8/2004 | Pless et al. |
| 2004/0176673 A1 | 9/2004 | Wahlstrand et al. |
| 2005/0003268 A1 | 1/2005 | Scott et al. |
| 2005/0004618 A1 | 1/2005 | Scott et al. |
| 2005/0010261 A1 | 1/2005 | Luders et al. |
| 2005/0015128 A1 | 1/2005 | Rezai et al. |
| 2005/0049646 A1 | 3/2005 | Luders et al. |
| 2005/0070458 A1 | 3/2005 | John |
| 2005/0075679 A1 | 4/2005 | Gliner et al. |
| 2005/0075680 A1 | 4/2005 | Lowry et al. |
| 2005/0092707 A1 | 5/2005 | Chantalat |
| 2005/0107753 A1 | 5/2005 | Rezai et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0222641 A1 | 10/2005 | Pless |
| 2005/0228249 A1 | 10/2005 | Boling |
| 2006/0129204 A1 | 6/2006 | Pless et al. |
| 2006/0190054 A1 | 8/2006 | Malinowski et al. |
| 2006/0190055 A1 | 8/2006 | Malinowski et al. |
| 2006/0212093 A1 | 9/2006 | Pless et al. |
| 2006/0224216 A1 | 10/2006 | Pless et al. |
| 2006/0229686 A1 | 10/2006 | Giftakis et al. |
| 2006/0247684 A1 | 11/2006 | Halperin et al. |
| 2007/0106143 A1 | 5/2007 | Flaherty |
| 2007/0150036 A1 | 6/2007 | Anderson |
| 2007/0173844 A1 | 7/2007 | Ralph et al. |
| 2007/0208352 A1 | 9/2007 | Henderson et al. |
| 2007/0225773 A1 | 9/2007 | Shen et al. |
| 2007/0233158 A1 | 10/2007 | Rodriguez |
| 2007/0233195 A1* | 10/2007 | Wahlstrand .......... A61N 1/3605 607/2 |
| 2007/0265683 A1 | 11/2007 | Ehrlich |
| 2008/0071313 A1 | 3/2008 | Stevenson et al. |
| 2008/0100061 A1 | 5/2008 | Sage et al. |
| 2008/0172068 A1 | 7/2008 | Adams et al. |
| 2008/0243219 A1 | 10/2008 | Malinowski et al. |
| 2008/0275466 A1 | 11/2008 | Skakoon |
| 2009/0112327 A1 | 4/2009 | Lane et al. |
| 2009/0118804 A1 | 5/2009 | Moffitt et al. |
| 2009/0157157 A1 | 6/2009 | Schorn et al. |
| 2009/0182351 A1 | 7/2009 | Malinowski et al. |
| 2009/0187149 A1 | 7/2009 | Nelson |
| 2009/0187222 A1 | 7/2009 | Barker |
| 2009/0202899 A1 | 8/2009 | Pyszczek |
| 2009/0246617 A1* | 10/2009 | Howard ................ H01M 2/263 429/161 |
| 2009/0276021 A1 | 11/2009 | Meadows et al. |
| 2010/0023020 A1 | 1/2010 | Barker et al. |
| 2010/0023100 A1 | 1/2010 | Barker |
| 2010/0076535 A1 | 3/2010 | Pianca et al. |
| 2010/0114249 A1 | 5/2010 | Wahlstrand et al. |
| 2010/0145357 A1 | 6/2010 | Lane et al. |
| 2010/0268298 A1 | 10/2010 | Moffitt et al. |
| 2010/0280585 A1 | 11/2010 | Appenrodt et al. |
| 2010/0312193 A1 | 12/2010 | Stratton et al. |
| 2011/0004267 A1 | 1/2011 | Meadows |
| 2011/0005069 A1 | 1/2011 | Pianca |
| 2011/0054563 A1 | 3/2011 | Janzig et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0190842 A1* | 8/2011 | Johnson ............... H01M 10/425 600/561 |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2012/0316628 A1 | 12/2012 | Lopez |
| 2013/0006410 A1 | 1/2013 | Gentile et al. |
| 2013/0066430 A1 | 3/2013 | Funderburk |
| 2013/0066431 A1 | 3/2013 | Funderburk |
| 2013/0105071 A1 | 5/2013 | Digiore et al. |
| 2013/0197424 A1 | 8/2013 | Bedenbaugh |
| 2013/0197602 A1 | 8/2013 | Pianca et al. |
| 2013/0304216 A1 | 11/2013 | Paspa et al. |
| 2014/0039587 A1 | 2/2014 | Romero |
| 2014/0257325 A1 | 9/2014 | Chavez et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0045864 A1 | 2/2015 | Howard |
| 2015/0051681 A1 | 2/2015 | Hershey |
| 2015/0066120 A1 | 3/2015 | Govea |

(56) References Cited

U.S. PATENT DOCUMENTS

| | | | |
|---|---|---|---|
| 2015/0073507 A1* | 3/2015 | Reinke | A61N 1/3787 607/61 |
| 2015/0151113 A1 | 6/2015 | Govea et al. | |
| 2016/0228692 A1 | 8/2016 | Steinke et al. | |
| 2019/0143125 A1 | 5/2019 | Funderburk et al. | |

FOREIGN PATENT DOCUMENTS

| | | |
|---|---|---|
| WO | 1998008554 | 3/1998 |
| WO | 1999055408 | 11/1999 |
| WO | 2000013743 | 3/2000 |
| WO | 20020045795 | 6/2002 |
| WO | 2003026738 | 4/2003 |
| WO | 20030028521 | 4/2003 |
| WO | 20040084749 | 10/2004 |
| WO | 2004105640 | 12/2004 |
| WO | 2005079903 | 9/2005 |
| WO | 2006031317 | 3/2006 |
| WO | 2008054691 | 5/2008 |
| WO | 2008054699 | 5/2008 |
| WO | 2008107815 | 9/2008 |
| WO | 2008107822 | 9/2008 |
| WO | 2008134509 | 11/2008 |
| WO | 2009055746 | 4/2009 |

OTHER PUBLICATIONS

Roberts DW, Hartov A. Kennedy FE, Miga MI, Paulsen KD: Intraoperative brain shift and deformation: A quantitative analysis of cortical displacement in 28 cases. Neurosurgery 43:749-760, 1998.

Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.

Nimsky C., Gansland 0., Cerny S., Hastreiter P, Greiner G., Fahlbusch R.: Quantification of, visualization of, and compensation for brain shift using intraoperative magnetic resonance imaging. Neurosurgery 47, 1070-1080, 2000.

Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76 (8): 1161-3, 2005.

Axelsson, Stefan et ai., Longitudinal cephalometric standards for the neurocranium in Norwegians from 6 to 21 years of age, European Journal of Orthodontics, vol. 25 (2003) pp. 185-198.

Lieberman, Daniel E. et al., Basicranial influence on overall cranial shape, Journal of Human Evolution, vol. 38 (2000) pp. 291-315.

* cited by examiner

SYSTEMS AND METHODS FOR MAKING AND USING AN ELECTRICAL STIMULATION SYSTEM WITH A CASE-NEUTRAL BATTERY

CROSS-REFERENCE TO RELATED APPLICATIONS

This application claims the benefit under 35 U.S.C. § 119(e) of U.S. Provisional Patent Application Ser. No. 62/617,992, filed Jan. 16, 2018, which is incorporated herein by reference.

FIELD

The present invention is directed to the area of implantable electrical stimulation systems and methods of making and using the systems. The present invention is also directed to stimulation systems with implantable control modules utilizing a case-neutral battery, as well as making and using the battery, control modules, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

In some aspects, a control module for an electrical stimulation system includes a sealed electronics housing; an electronic subassembly disposed within the electronics housing; one or more connector assemblies coupled to the electronic subassembly; and a rechargeable battery disposed external to the electronics housing. The one or more connector assemblies are configured to receive a lead. The rechargeable battery includes a positive electrode, a negative electrode, and a single battery case attached directly to the sealed electronics housing and forming a sealed cavity that encapsulates both the positive electrode and the negative electrode. The battery case is electrically isolated from each of the positive electrode and the battery electrode.

In at least some embodiments, the battery case forms a hermetic seal around the positive electrode and the negative electrode. In at least some embodiments, the battery case is attached to the electronics housing via at least one of a weld or adhesive. In at least some embodiments, the battery case includes a cap attached to the electronics housing and electrically isolating the positive and negative electrodes. In at least some embodiments, the positive electrode and the negative electrode extend through the cap.

In at least some embodiments, the positive electrode includes a positive terminal and the negative electrode includes a negative terminal. In at least some embodiments, the positive terminal is formed from different material than the positive electrode, or the negative terminal is formed from different material than the negative electrode, or both.

In at least some embodiments, the control module further includes a first feedthrough and a second feedthrough extending through the sealed electronics housing, where the first feedthrough is electrically coupled to the positive electrode and the second feedthrough is electrically coupled to the negative electrode. In at least some embodiments, the control module further includes a covering disposed over at least a portion of each of the electronics housing and the one or more connector assemblies.

In at least some embodiments, the battery case is configured to directly contact patient tissue when implanted into a patient. In at least some embodiments, the battery case is configured to directly contact a bony structure when implanted into a patient. In at least some embodiments, the battery case is coated with at least one of silicone or parylene.

In at least some embodiments, each of the one or more connector assemblies includes a connector lumen configured to receive a lead, and connector contacts arranged along the connector lumen and in electrical communication with the electronic subassembly.

In other aspects, an electrical stimulation system includes any of the above-described embodiments of the control module; and an electrical stimulation lead coupleable to the control module via the one or more connector assemblies of the control module.

In yet other aspects, a method for implanting a control module of an electrical stimulation system along a patient's skull includes providing any of the above-described embodiments of the control module. A recess is formed along an outer surface of the patient's skull. The control module is placed along the skull with the battery of the control module inserted into the recess. The control module is attached to the skull.

In at least some embodiments, providing the control module includes providing the control module with the battery case coated with at least one of parylene or silicone. In at least some embodiments, the method further includes coating the battery with silicone prior to attaching the control module to the skull. In at least some embodiments, placing the control module along the skull with the battery of the control module inserted into the recess includes placing the control module along the skull with at least a portion of the electronics housing extending from the recess. In at least some embodiments, attaching the control module to the skull includes at least one of adhering the control module to the skull using bone cement or fastening the control module to the skull using one or more fasteners.

In still yet other aspects, a method of charging a rechargeable battery of a control module of an electrical stimulation system implanted along a patient's skull includes providing any of the above-described embodiments of the control module. A recess is formed along an outer surface of the skull. The control module is placed along the skull with the battery of the control module inserted into the recess, thereby surrounding portions of the battery extending from the control module with bone cells, the bone cells having a heat tolerance. The control module is attached to the skull.

The battery is inductively charged at a charging rate limited by the heat tolerance of the bone cells surrounding the battery.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to stimulation systems with implantable control modules utilizing a case-neutral battery, as well as making and using the battery, control modules, and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
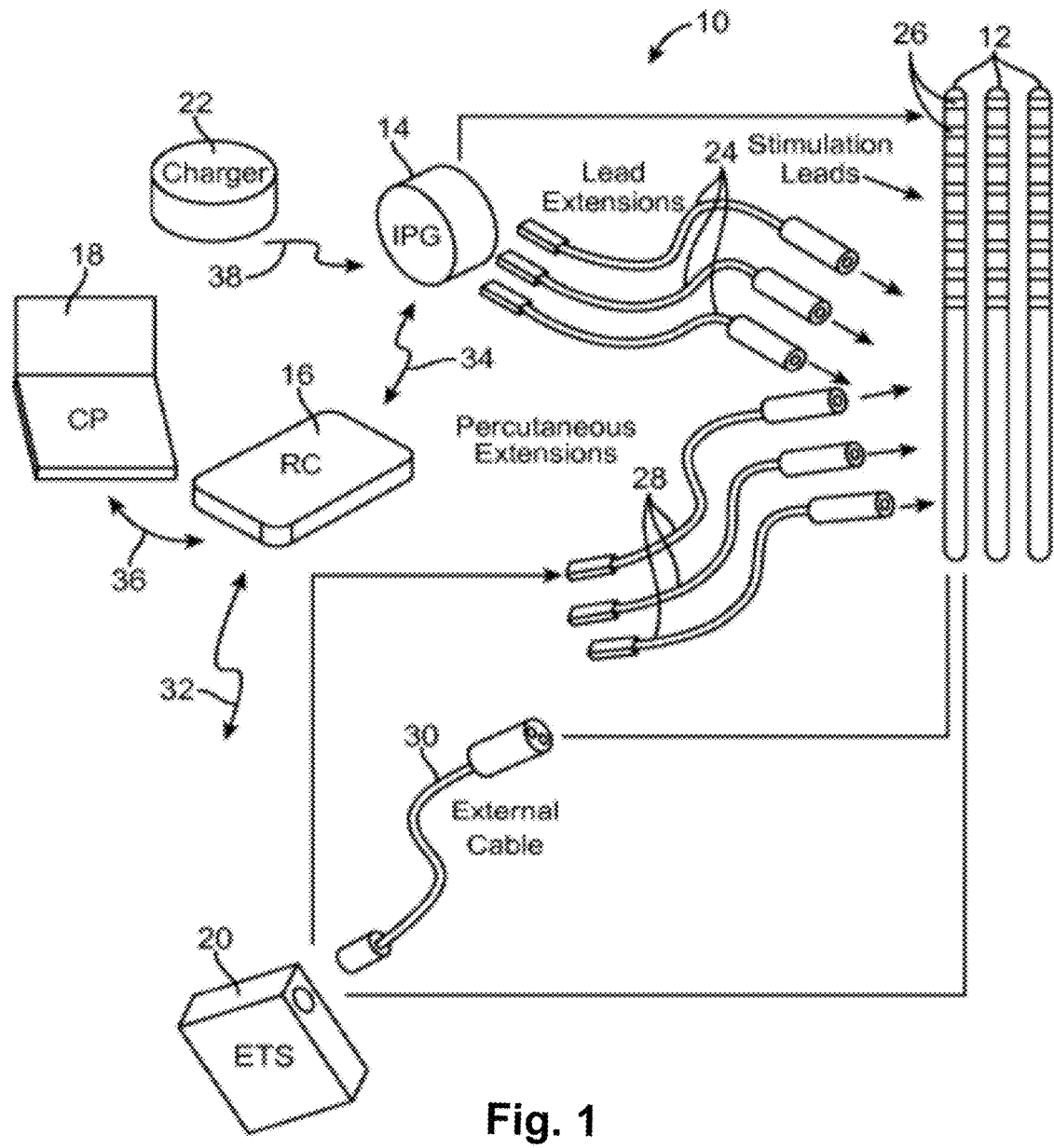
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
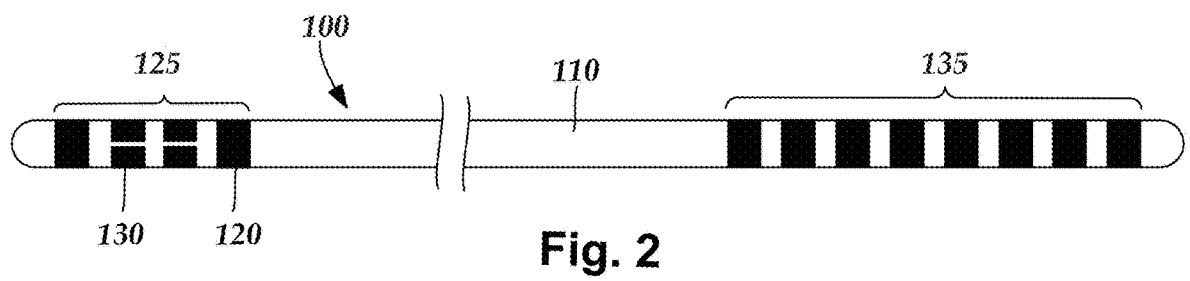
FIG. 2 is a schematic side view of one embodiment of an electrical stimulation lead, according to the invention.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. It will be understood that the leads could include any suitable number of electrodes. It will be understood that the leads can include any suitable number of electrodes including, for example, distal-tip electrodes, or one or more segmented electrodes, and ring electrodes.

FIG. 2 illustrates one embodiment of a lead 110 with electrodes 125 disposed at least partially about a circumference of the lead 110 along a distal end portion of the lead and terminals 135 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 125 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
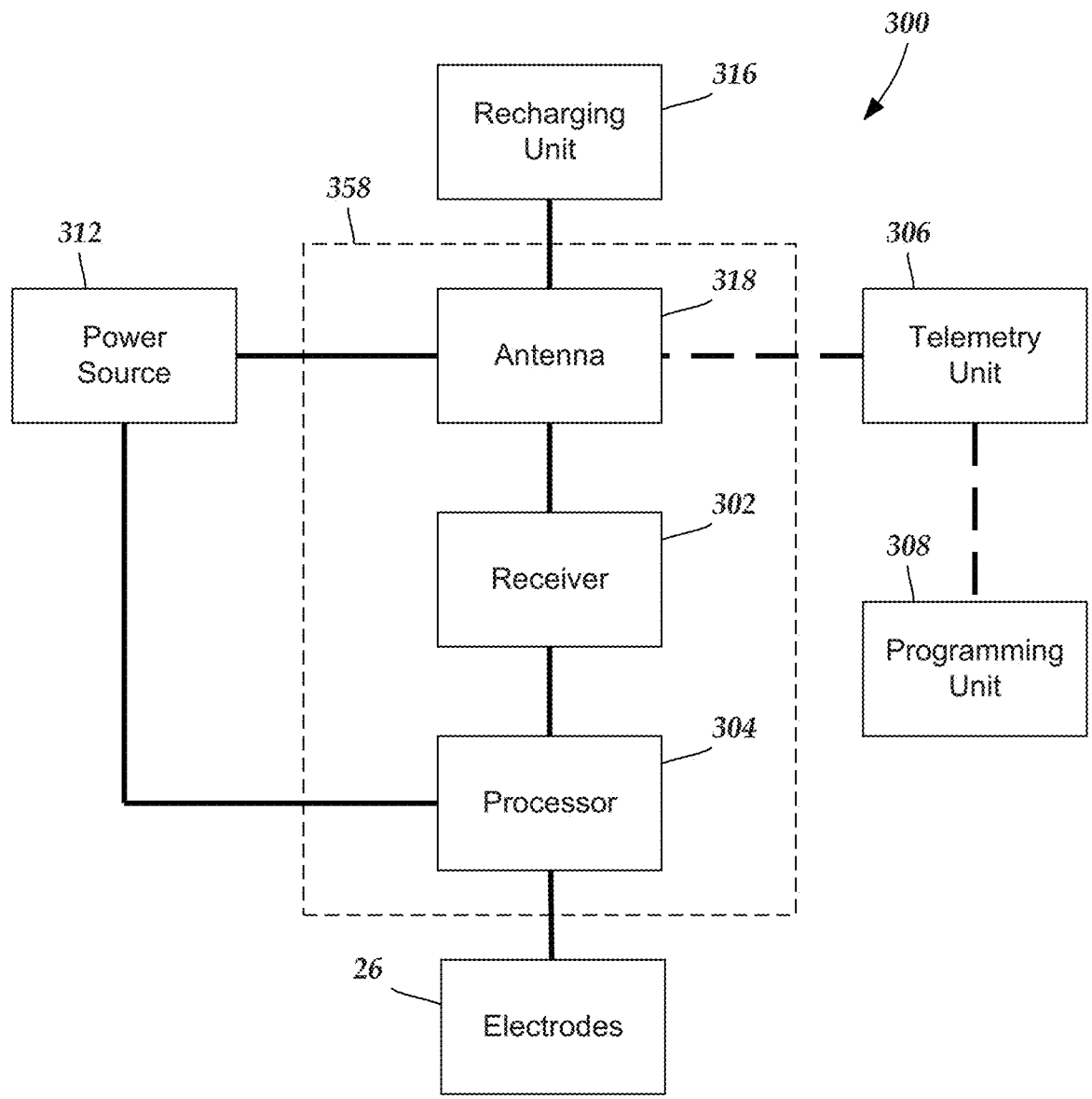
FIG. 3 is a schematic overview of one embodiment of components of a stimulation system, including an electronic subassembly disposed within a control module, according to the invention.

FIG. 3 is a schematic overview of one embodiment of components of an electrical stimulation system 300 including an electronic subassembly 358 disposed within a control module. The electronic subassembly 358 may include one or more components of the IPG. It will be understood that the electrical stimulation system can include more, fewer, or different components and can have a variety of different configurations including those configurations disclosed in the stimulator references cited herein.

Some of the components (for example, one or more antennas 318, a receiver 302, and a processor 304) of the electrical stimulation system can be positioned on one or more circuit boards or similar carriers within a sealed electronics housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. In at least some embodiments, the antenna 318 (or the secondary antenna) is implemented using the auxiliary electrically-conductive conductor. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above. The electronic subassembly 358 and, optionally, the power source 312 can be disposed within a control module (e.g., the IPG 14 or the ETS 20 of FIG. 1).

In one embodiment, electrical stimulation signals are emitted by the electrodes (e.g., 26 in FIG. 1) to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

Figure 4A:
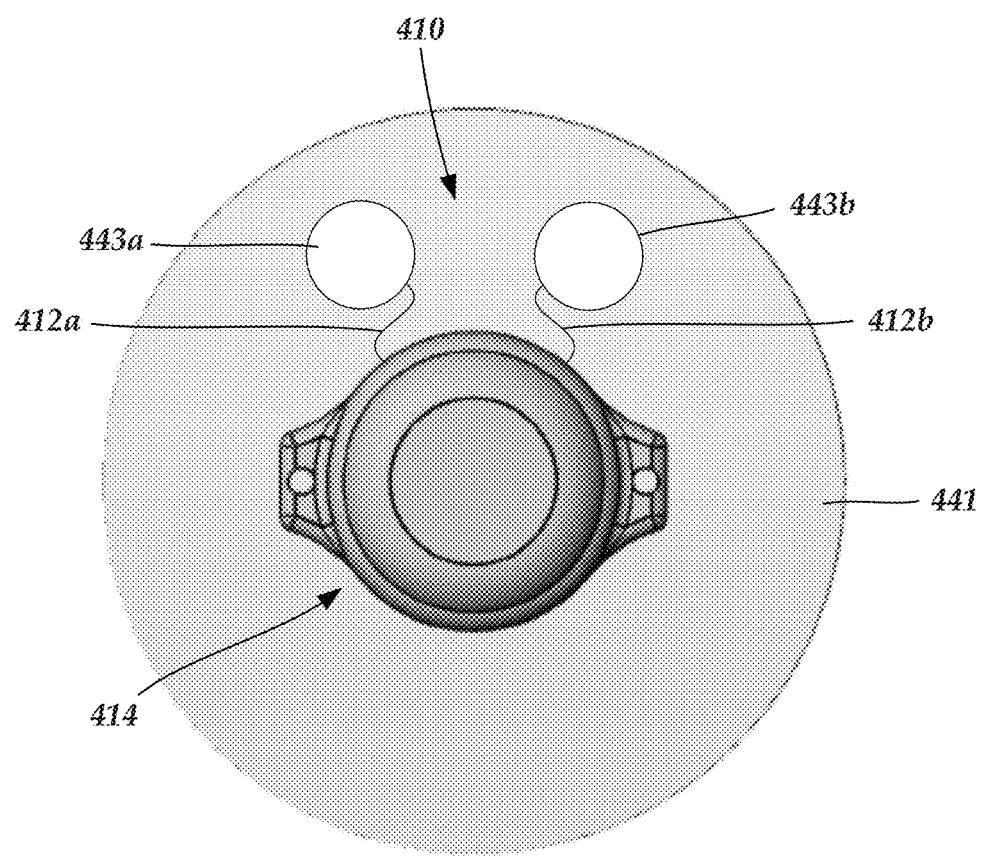
FIG. 4A is a schematic top view of one embodiment of a low-profile control module disposed along an outer surface of a skull and two leads extending from the control module and into the skull via burr holes formed in the skull, the burr holes covered with burr-hole covers, according to the invention.
Figure 4B:
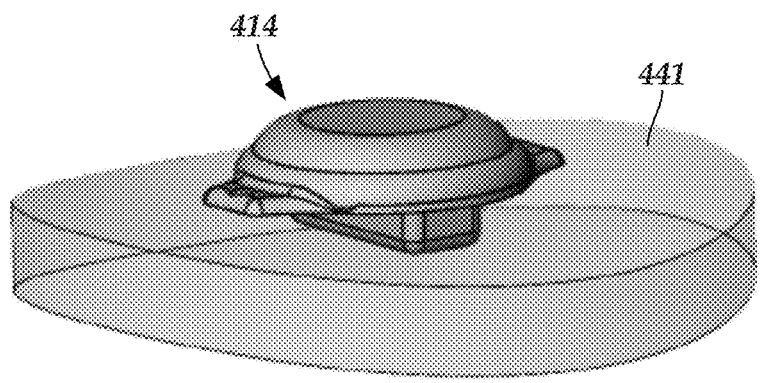
FIG. 4B is a schematic perspective view of one embodiment of the low-profile control module of FIG. 4A disposed along a portion of an outer surface of the skull of FIG. 4A with a portion of the control module inset into the skull, according to the invention.

Turning to FIGS. 4A-4B, conventional control modules (e.g., IPG 14) include electronics, connector assemblies and, in particular, power sources (e.g., batteries) that collectively create a size and shape that may limit the locations where the control module can be implanted. In some instances, the size or shape of a control module may prevent the control module from physically fitting within a desired implantation location. In other instances, although a control module may physically fit within a desired implantation location, the size or shape of the control module may result in an undesirable cosmetic issue, such as the control module causing visible bulging of patient tissue.

In the case of deep brain stimulation, leads are typically extended through burr holes drilled into the patient's skull. In some instances, due to limited space in the patient's head external to the skull the control module is implanted below the patient's clavicle area. In which case, one or more leads are tunneled along the patient's neck from the burr hole(s) to the clavicle. Forming such tunnels can be risky and undesirable for the patient.

Instead, it may be advantageous to implant the control modules over the patient's skull and beneath the patient's scalp, thereby obviating the need to tunnel leads along the patient's neck. The amount of space between the patient's skull and scalp, however, may prevent a conventional control module from fitting over the patient's skull. In some instances, although it may be possible to position the control module over the patient's skull, the patient is consequently burdened with one or more unsightly bulges extending from his or her head.

As described above with reference to FIGS. 1-3, an implantable control module (e.g., IPG 14 of FIG. 1) may include a rechargeable battery (e.g., power source 312 of FIG. 3) that is rechargeable via a charger (e.g., charger 22 of FIG. 1) positioned external to the patient in proximity to the battery. One technique for recharging the battery of a control module when the control module is implanted in a patient includes using a charger to inductively recharge the control module battery. For example, the charger may include a coil that generates a magnetic charging field that induces a current within a coil within the control module which, in turn, charges the control module battery.

It may be advantageous to charge the control module battery as quickly as possible. A patient with an implanted control module may undergo many charging sessions over the lifespan of the implanted device. Reducing the amount of time needed to recharge the control module battery may enable patients to live a more active lifestyle and reduce inconveniences associated with regularly recharging an implanted device utilizing a battery.

Inductively recharging the control module battery may generate heat in the battery, thereby undesirably heating nearby patient tissue. The amount of heat generated may have a positive correlation with the rate of the recharge. In other words, increasing the charging rate of the battery may increase the amount of heat generated. Accordingly, patient safety may dictate that the charging rate of the battery be limited to the heat tolerance of patient tissue in proximity to the battery. Thus, the amount of heat that can be safely generated in patient tissue in proximity to the battery may depend, at least in part, on the type of tissue in proximity to the battery.

As described herein, a control module with a case-neutral battery can be implanted into a patient. Such a design may increase the number of locations within a patient where a control module is implantable, as compared to conventional control modules. Furthermore, such a design may also improve patient cosmetic outlooks post-implantation, by reducing undesirable bulging of patient tissue caused by the control module, as compared to conventional control modules.

For illustrative purposes, the control module described herein is used for deep brain stimulation. It will be understood, however, that a control module with a case-neutral battery can be used for applications other than deep brain stimulation, including peripheral nerve stimulation (e.g., occipital nerve stimulation, pudendal nerve stimulation, or the like), spinal cord stimulation, dorsal root ganglion stimulation, sacral nerve stimulation, or stimulation of other nerves, muscles, and tissues.

In at least some embodiments, the control module is suitable for disposing over the patient's skull and beneath the patient's scalp. In at least some embodiments, when mounted to an outer surface of a patient's skull, the control module extends radially outwardly from the outer surface of the skull by no more than 10 mm, 9 mm, 8 mm, 7 mm, 6 mm, 5 mm, 4 mm, or 3 mm. In at least some embodiments, the control module extends radially outwardly from the outer surface of the skull by no less than 4 mm and no more than 7 mm. In at least some embodiments, the control module extends radially outwardly from the outer surface of the skull by no less than 5 mm and no more than 6 mm.

The below-described control module with a case-neutral battery reduces a height dimension of the control module, as compared to conventional control modules, at least in part by utilizing an electrically-isolated case. In conventional control modules, the outer surface ("case") of the battery is electrically coupled to either the positive or negative battery electrode. Accordingly, an additional, electrically-uncharged outer shell is typically disposed over the battery case to prevent undesired contact of the charged case with patient tissue. In some instances, the outer shell may be the electronics housing.

In contrast, the outer surface of a case-neutral battery is electrically isolated from both the positive and negative battery electrodes. Therefore, the case-neutral battery does not require an outer shell to be disposed around the battery to prevent an electrode-coupled surface of the battery from contacting patient tissue. Accordingly, the volume of a case-neutral battery may be reduced from conventional batteries without sacrificing battery capacity by removing the outer shell.

The distance that the control module extends outwardly from the skull may be further reduced by insetting a portion of the control module into a recess carved into the patient's skull. In some embodiments, the case-neutral control module is configured and arranged so that the portion of the control module disposed within the recess includes the battery.

The skull may tolerate higher temperatures than other patient tissues (e.g., subcutaneous tissues disposed thereover). At least one study has shown that subcutaneous cells, such as patient tissue disposed over the patient's skull, may become susceptible to necrosis when exposed to prolonged, elevated temperatures of 43°-45° C. In contrast, at least one study has shown that bone cells may resist becoming susceptible to necrosis until exposed to prolonged, elevated temperatures of 47° C. Thus, bone tissue may be able to safely tolerate temperatures 2°-4° C. higher than subcutaneous tissue.

Accordingly, it may be advantageous to dispose the battery within the recess of the skull to increase temperature tolerance, as compared to disposing the battery over top of the skull. Increased temperature tolerance, in turn, may enable the rate of charging of the battery to be safely increased from the rate of charging available when the battery of the control module is disposed over the skull.

For illustrative purposes, the skull is described as an implantation location. It will be understood, however, that the same, or similar, advantages may also be achievable in other bony structures, such as the sacrum.

Figure 4C:
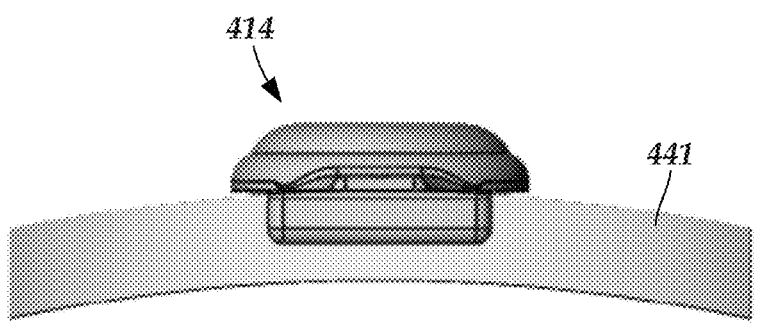
FIG. 4C is a schematic side view of one embodiment of the low-profile control module of FIG. 4A disposed along a cross-sectional view of a portion of an outer surface of the skull of FIG. 4A with a portion of the control module inset into the skull, according to the invention.

FIG. 4A shows, in top view, one embodiment of an electrical stimulation system 410 that includes a control module 414 disposed along an outer surface of a skull 441. Two leads 412a, 412b extend from the control module 414 and into the skull 441 via burr holes formed in the skull, over which burr hole covers 443a, 443b, respectively, are disposed. FIG. 4B shows the control module 414 and a portion of the skull 441 in perspective view. FIG. 4C shows the control module 414 (shown in side view) disposed along a portion of the skull 441 (shown in cross-sectional view).

Note that, two leads are shown in the electrical stimulation systems shown in FIG. 4A. It will be understood that, electrical stimulation systems can have any suitable number of leads including, for example, one, two, three, four, five, six, seven, eight, or more leads. In the case of deep brain stimulation, the one or more leads can be extended through the skull via any suitable number of burr holes including, for example, one, two, three, four, five, six, seven, eight, or more burr holes.

Figure 5A:
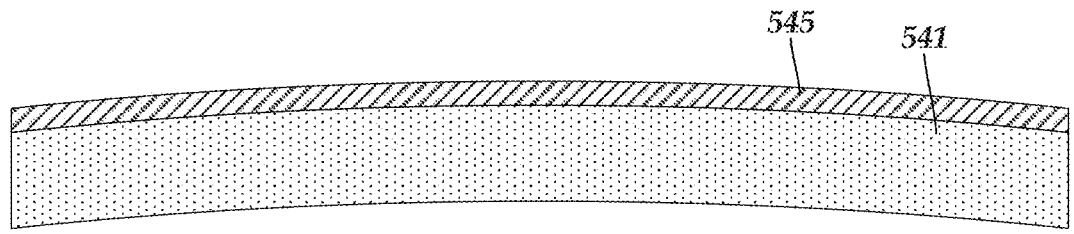
FIG. 5A is a schematic cross-sectional view of a portion of a patient's head that includes a skull with a scalp disposed over an outer surface of the skull.
Figure 5B:
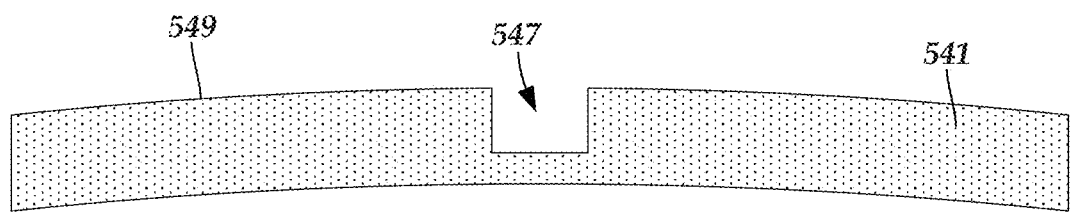
FIG. 5B is a schematic cross-sectional view of the portion of the skull shown in FIG. 5A with the overlaid scalp of FIG. 5A peeled away to expose the outer surface of the skull and a recess formed therein suitable for receiving a portion of the control module of FIGS. 4A-4C, according to the invention.

FIG. 5A shows, in schematic cross-sectional view, a portion of a patient's head that includes a scalp 545 disposed over a skull 541. FIG. 5B shows, in schematic cross-sectional view, the portion of the patient's skull 541 shown in FIG. 5A. In FIG. 5B, the scalp (545 in FIG. 5A) is removed (e.g., peeled back) and a recess 547 is carved into an outer surface 549 of the skull. As will be described below, the recess can be sized and shaped to accommodate a portion of the control module that includes the battery.

Figure 6:
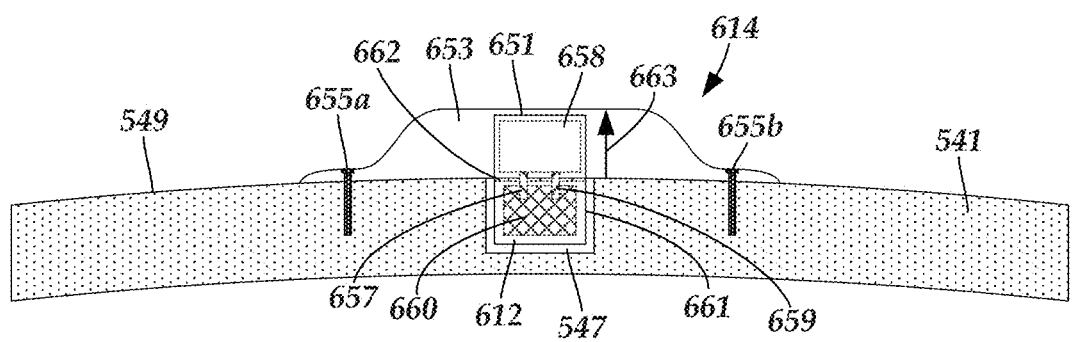
FIG. 6 is a schematic cross-sectional view of one embodiment of the control module of FIGS. 4A-4C attached to the skull of FIG. 5B with a battery of the control module disposed in a recess formed in the skull, according to the invention.

FIG. 6 shows, in a schematic cross-sectional view, one embodiment of the control module 414 disposed over the skull 541. The control module 414 includes an electronic subassembly 658 disposed in an electronics housing 651 and a case-neutral battery 612 ("battery") external to the electronics housing 651 and coupled to the electronic subassembly 658. The electronics housing is sealed. In at least some embodiments, the electronics housing is hermetically sealed. The battery abuts the electronic housing.

The battery includes a positive electrode 657 and a negative electrode 659 both extending from within an electrolyte 660 disposed within a case 661 to the electronic subassembly 658. The positive electrode 657 and the negative electrode 659 are both electrically isolated from the case 661. The case seals the electrodes 657, 659 from the environment external to the case; and reduces, or even eliminates, current leakage from the electrodes 657, 659. In at least some embodiments, the battery case hermetically seals the electrodes 657, 659.

In FIG. 6, the positive and negative electrodes are shown arranged in a side-by-side arrangement. The arrangement shown in FIG. 6 is not meant to be limiting, as the positive and negative electrodes can be arranged relative to one another with the case in any suitable configuration. The positive and negative electrodes are isolated from the case and include positive and negative terminals, respectively, that electrically couple to the electronic subassembly. In some embodiments, the positive and negative terminals are formed from the same material as their respective electrodes. In other embodiments, the positive and negative terminals are formed from one or more different materials than their respective electrodes. In at least some embodiments, one of the positive and negative terminals is formed from the same material as their respective electrodes while the other of the positive and negative terminals is formed from one or more different materials than their respective electrodes.

The non-electrode portions of the battery that contact the electronics housing can be attached directly to the electronics housing using any suitable technique including, for example, welding, adhesive, or combinations thereof. In some embodiments, the battery case 661 is open to the electronics housing 651 along a wall of the electronics housing through which the electrodes 657,659 extend (e.g., via feedthroughs) and to which the battery case 661 is attached. In other embodiments, the battery case 661 includes an optional cap 662 through which the electrodes 657, 659 extend. In at least some embodiments, the cap is electrically isolated from the electrodes 657, 659 and the electrodes extend through the cap via feedthroughs.

Electrically isolating the case 661 from each of the positive and negative electrodes may enable the height dimension 663 of the control module (i.e., how far the control module extends outwardly from the skull) to be reduced from the height dimension of conventional control modules. Electrically isolating the case 661 from each of the positive and negative electrodes obviates the need for a secondary outer shell to be disposed over the battery case, as is typically done with conventional batteries in control modules. Depending on what types of materials are used for a secondary outer shell, eliminating the secondary outer shell may enable the height dimension of the control module to be reduced by approximately 0.04-0.05 inches (0.10-0.13 cm).

Disposing a portion of the control module in the recess may further reduce the height dimension 657 of the control module by placing a portion of the control module beneath the outer surface 549 of the skull, thereby reducing some of the bulk of the control module disposed over the skull. It may be particularly advantageous to dispose all, or at least a majority (e.g., 50%, 60%, 70%, 80%, 90%, or more of an outer surface of the case 661), of the battery within the recess (as shown in FIG. 6). Disposing the battery of the control module in the recess may also have the advantage of enabling the charging rate of the battery to be safely increased from what a safe rate of charge for the battery would be were the battery to be disposed in subcutaneous tissue over the skull.

As mentioned above, inductively recharging the battery may generate heat in the battery, thereby also undesirably heating nearby patient tissue. Thus, the charging rate of the battery may be limited to the heat tolerance of patient tissue in proximity to the control module. Accordingly, the amount of heat that can be safely generated in patient tissue in proximity to the control module battery may depend, at least in part, on the type of tissue heated.

As also mentioned above, bone tissue may be able to safely tolerate temperatures 2°-4° C. higher than subcutaneous tissue. Accordingly, it may be advantageous to dispose the battery within the recess to increase temperature tolerance, as compared to disposing the battery over top of the skull. Increased temperature tolerance, in turn, may enable the charging rate of the battery to be safely increased from the rate of charging rate of the battery were the battery disposed over the skull.

In FIG. 6 (and in other figures), the control module also includes an optional covering 653 disposed over at least a portion of the control module. In some embodiments, the covering is electrically nonconductive and forms a seal to insulate electrical components from one another and/or the patient. The covering can be formed from any suitable biocompatible material. In some embodiments, the covering is formed from a thermoplastic polymer, such as polyether ether ketone. In some embodiments, the covering is made via an overmolding process. In at least some embodiments, the covering is disposed over the electronics housing 651.

In at least some embodiments, the control module includes a charging coil coupled to the electronic subassembly. In at least some embodiments, the control module includes one or more antennas (e.g., Bluetooth, or the like) coupled to the electronic subassembly. In at least some embodiments, the charging coil and antenna(s) are disposed external to the electronics housing. In at least some embodiments, the charging coil and antenna(s) are disposed beneath, or embedded within, the covering.

The control module is typically attached to the skull to prevent undesired migration of all, or a portion, of the control module. In some embodiments, one or more fasteners (e.g., screws, pins, or the like) are used for fastening the control module to patient tissue. In FIG. 6 (and in other figures), fasteners 655a, 655b are shown formed as bone screws fastened to the skull. The fasteners can be extended through any suitable portion of the control module to attach the control module to the skull. In FIG. 6 (and in other figures), the fasteners extend through apertures defined along opposing portions of the covering. Any suitable number of fasteners can be used to attach the control module to the skull including, for example, one, two, three, four, five, six, or more fasteners.

Figure 7A:
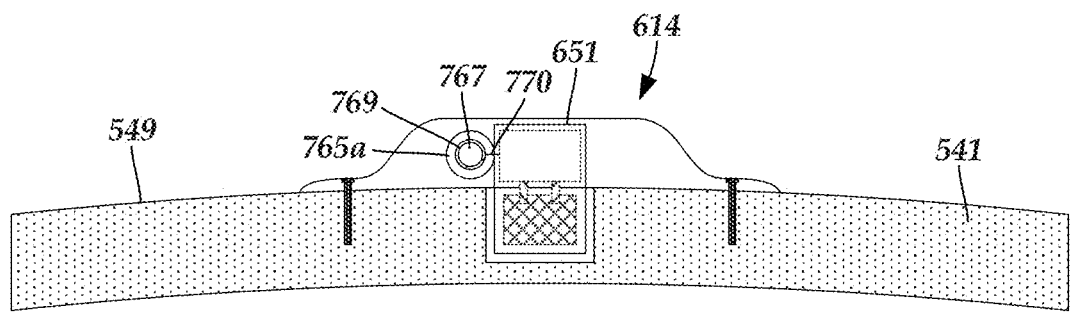
FIG. 7A is a schematic cross-sectional of one embodiment of the control module of FIG. 6 attached to the skull of FIG. 6 with a connector assembly disposed along one side of the electronics housing of the control module, according to the invention.
Figure 7B:
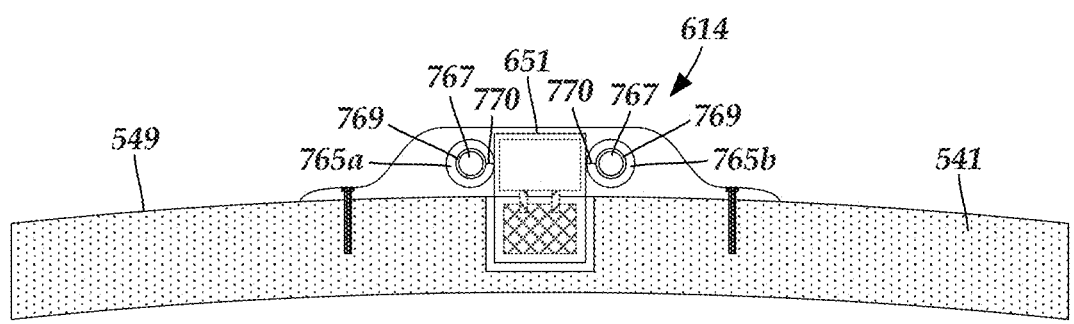
FIG. 7B is a schematic cross-sectional of one embodiment of the control module of FIG. 6 attached to the skull of FIG. 6 with connector assemblies disposed along opposing sides of the electronics housing of the control module, according to the invention.
Figure 7C:
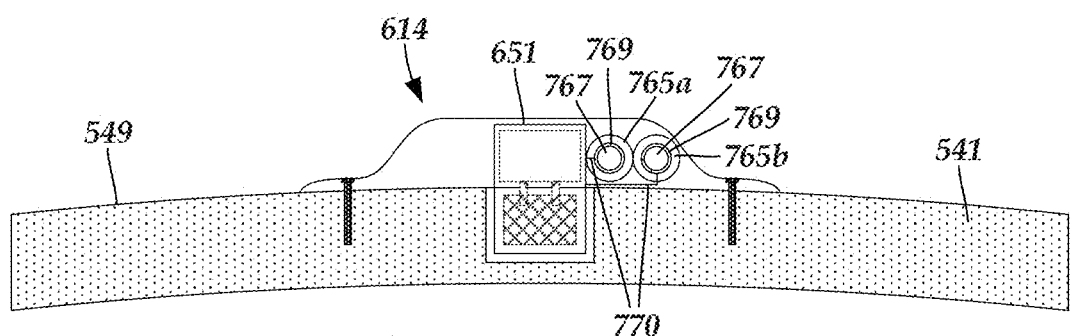
FIG. 7C is a schematic cross-sectional of one embodiment of the control module of FIG. 6 attached to the skull of FIG. 6 with connector assemblies disposed along one side of the electronics housing of the control module, according to the invention.

Turning to FIGS. 7A-7C, the control module 414 may further include one or more connector assemblies coupled to the electronic subassembly. The connector assemblies are configured to receive one or more leads. The one or more leads typically extend from the control module to a target stimulation location where stimulation generated by the control module is delivered to patient tissue.

In some embodiments, the control module includes a single connector assembly. In other embodiments, the control module includes multiple connector assemblies. In the illustrated embodiments, each connector assembly is configured and arranged to receive a single lead.

FIGS. 7A-7C each shows, in schematic cross-sectional view, a different embodiment of the control module 414 disposed over the skull 541. In FIG. 7A, the control module 414 includes a single connector assembly 765a. In FIG. 7B, the control module includes two connector assemblies 765a, 765b, where the connector assemblies are disposed along opposing sides of the electronics housing 651 from one other. In FIG. 7C, the control module includes two connector assemblies 765a, 765b, where each of the connector assemblies is disposed along the same side of the electronics housing 651.

Each of the connector assemblies defines a connector lumen 767 configured to receive a proximal portion of a lead. Connector contacts, such as connector contact 769, are arranged along each of the connector lumens and are electrically coupled to the electronic subassembly via one or more connector conductors 770. The connector contacts 769 couple with terminals of the leads when the proximal portions of the leads are received by the connector assemblies. The connector contacts can be electrically isolated from one another by electrically-nonconductive spacers. The connector assemblies may, optionally, include end stops to promote alignment of the lead terminals with the connector contacts. In at least some embodiments, the covering 653 is disposed over at least a portion of the one or more connector assemblies.

The connector assemblies are disposed external to the electronics housing and the battery. The placement of the connector assemblies relative to the electronics housing 651 can be determined based on any number of different factors including, for example, the positioning of the one or more target stimulation locations relative to the control module, the anatomy of the location where the control module is implanted, or the like. It will be understood that the number of connector assemblies and the positioning of the one or more connector assemblies relative to the electronics housing may influence the overall shape and size of the control module along one or more dimensions orthogonal to the height dimension (663 in FIG. 6).

Figure 8A:
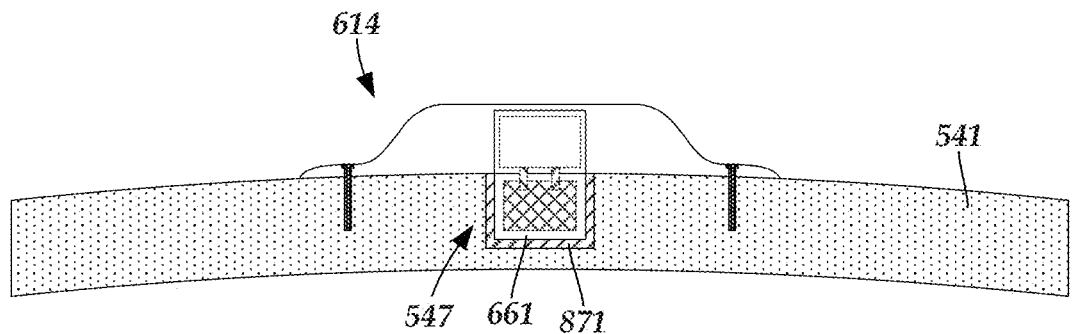
FIG. 8A is a schematic cross-sectional of one embodiment of the control module of FIG. 6 attached to the skull of FIG. 6 with the battery of the control module coated with silicone, according to the invention.
Figure 8B:
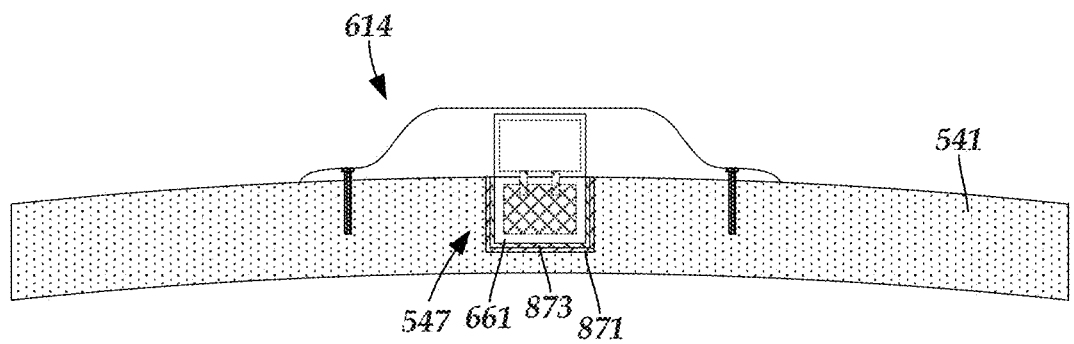
FIG. 8B is a schematic cross-sectional of one embodiment of the control module of FIG. 6 attached to the skull of FIG. 6 with the battery of the control module coated with a parylene and silicone, according to the invention.
Figure 8C:
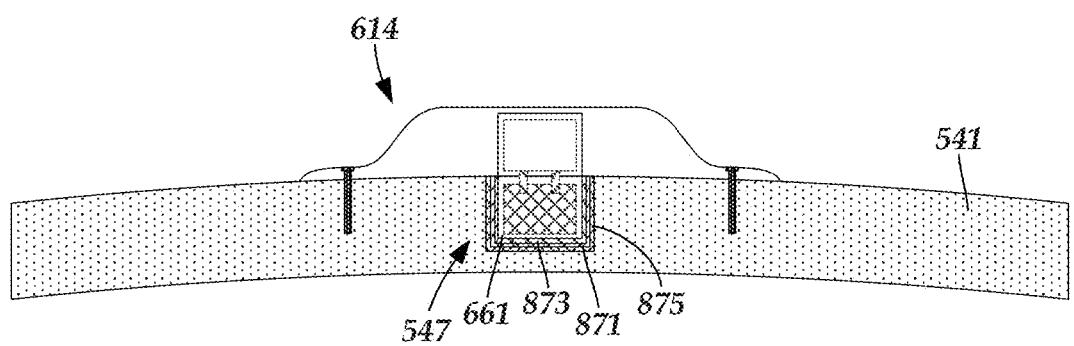
FIG. 8C is a schematic cross-sectional of one embodiment of the control module of FIG. 6 attached to the skull of FIG. 6 with the battery of the control module coated with a parylene, silicone, and bone cement, according to the invention.

Turning to FIGS. 8A-8C, implantation of the control module includes placement of a portion of the control module (e.g., the battery) in a recess formed in a bony structure (e.g., a skull). In some embodiments, a template is used to facilitate estimation of the recess dimensions needed to accommodate the portion of the control module to be inset into the recess. For example, a mold (e.g., a silicone mold) can be formed with the same size and shape as the portion of the control module to be inset into the recess. The mold can then be used by a medical practitioner to test the dimensions of the recess during formation. Once the dimensions of the recess are sufficient for snugly fitting the mold, the mold can be removed from the recess and the control module can be implanted.

Once the recess is completed, the control module is positioned over the recess, with the desired portion of the control module (e.g., the battery) disposed in the recess, and the control module is fastened to the bony structure. In at least some embodiments, the battery is partially disposed in the recess. In at least some embodiments, at least 50%, 60%, 70%, 80%, 90% of the battery is disposed in the recess. In at least some embodiments, the entire battery is disposed in the recess.

In some embodiments, the portion of the control module (e.g., the battery) disposed in the recess is disposed directly against patient bone tissue (see e.g., FIG. 6). In other embodiments, one or more layers of one or more materials are disposed between the portion of the control module (e.g., the battery) disposed in the recess and the bone forming the walls (and floor, if applicable) of the recess. In some embodiments, the one or more layers of one or more materials are additionally disposed along other portions of the control module. In some embodiments, the one or more layers of one or more materials are disposed over the entire control module.

FIG. 8A shows, in a schematic cross-sectional view, one embodiment of the control module 414 disposed over the skull 541 with the battery 661 of the control module disposed in the recess 547 formed in the skull. As shown in FIG. 8A, the battery is coated with a layer of silicone 871 so that the silicone is disposed between the battery and the recess when the battery is disposed in the recess. The silicone may solidify over time and fill in any unreacted void spaces and reduce the risk of the patient developing an infection. It may also be advantageous to coat the entire control module with silicone, or any portion of the control module that contacts bone, including portions of the control module that are external to the recess, if applicable.

FIG. 8B shows, in a schematic cross-sectional view, one embodiment of the control module 414 disposed over the skull 541 with the battery 661 of the control module disposed in the recess 547 formed in the skull. As shown in FIG. 8B, the battery is coated with parylene 837 and silicone 871 so that the parylene and silicone are disposed between the battery and the recess when the battery is disposed in the recess. Parylene is chemically and biologically inert and has a low dielectric constant. Accordingly, it may be advantageous to coat the battery with parylene to improve one or more of the electrical, mechanical, and chemical properties of the battery. In some embodiments, the one or more portions (or the entire outer surface) of the control module is coated with parylene. In some embodiments, the control module is pre-coated with parylene and/or silicone prior to an implantation procedure.

FIG. 8C shows, in a schematic cross-sectional view, one embodiment of the control module 414 disposed over the skull 541 with the battery 661 of the control module disposed in the recess 547 formed in the skull. As shown in FIG. 8C, the battery is coated with parylene 873 and silicone 871 so that the parylene and silicone are disposed between the battery and the recess when the battery is disposed in the recess. FIG. 8C additionally shows bone cement 875 disposed between the battery and the recess, in addition to parylene and silicone. In alternate embodiments, only one of parylene or silicone is disposed between the control module and the bone cement.

It may be advantageous to coat one or more portions of the control module that abut the skull (e.g., the battery) with bone cement to facilitate attachment of the control module to the bony structure. The bone cement can be used either in addition to, or in lieu of, one or more fasteners. It may also be advantageous to coat one or more portions of the control module that abut the skull (e.g., the battery) with bone cement to fill in any unreacted void spaces and reduce the risk of the patient developing an infection. Should subsequent explanation of the control module become necessary, the silicone and parylene can, optionally, be broken using a tool, such as a scalpel.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method of charging a rechargeable battery of a control module of an electrical stimulation system implanted along a patient's skull, the method comprising:
   providing a control module comprising
      a sealed electronics housing,
      an electronic subassembly disposed within the sealed electronics housing,
      one or more connector assemblies coupled to the electronic subassembly, the one or more connector assemblies configured and arranged to receive a lead, and
      a rechargeable battery disposed external to the sealed electronics housing, the rechargeable battery comprising
         a positive electrode,
         a negative electrode, and
         a single battery case attached directly to the sealed electronics housing and forming a sealed cavity that encapsulates both the positive electrode and the negative electrode, the single battery case electrically isolated from each of the positive electrode and the negative electrode;
   forming a recess along an outer surface of the skull;
   placing the control module along the skull with the rechargeable battery of the control module inserted into the recess, thereby surrounding portions of the rechargeable battery extending from the control module with bone cells, the bone cells having a heat tolerance;
   attaching the control module to the skull; and inductively charging the rechargeable battery at a charging rate limited by the heat tolerance of the bone cells surrounding the rechargeable battery.

2. The method of claim 1, wherein the control module further comprises a positive terminal coupled to the positive electrode and a negative terminal coupled to the negative electrode.

3. The method of claim 2, wherein the positive terminal is formed from different material than the positive electrode, or the negative terminal is formed from different material than the negative electrode, or both.

4. The method of claim 1, wherein the single battery case comprises a cap attached to the sealed electronics housing and electrically isolating the positive and negative electrodes.

5. The method of claim 4, wherein the positive electrode and the negative electrode extend through the cap.

6. The method of claim 1, wherein the single battery case forms a hermetic seal around the positive electrode and the negative electrode.

7. The method of claim 1, wherein the single battery case is attached to the sealed electronics housing via at least one of a weld or adhesive.

8. The method of claim 1, wherein the control module further comprises a first feedthrough and a second feedthrough extending through the sealed electronics housing, the first feedthrough electrically coupled to the positive electrode and the second feedthrough electrically coupled to the negative electrode.

9. The method of claim 1, wherein the single battery case is configured and arranged to directly contact patient tissue when implanted into a patient.

10. The method of claim 1, wherein the single battery case is configured and arranged to directly contact a bony structure when implanted into a patient.

11. The method of claim 1, wherein the control module further comprises a covering disposed over at least a portion of each of the sealed electronics housing and the one or more connector assemblies.

12. The method of claim 1, wherein each of the one or more connector assemblies comprises:
a connector lumen configured and arranged to receive a lead, and
a plurality of connector contacts arranged along the connector lumen and in electrical communication with the electronic subassembly.

13. The method of claim 1, wherein providing the control module comprises providing the control module with the single battery case coated with at least one of parylene or silicone.

14. The method of claim 1, further comprising coating the rechargeable battery with silicone prior to attaching the control module to the skull.

15. The method of claim 1, wherein placing the control module along the skull with the rechargeable battery of the control module inserted into the recess comprises placing the control module along the skull with at least a portion of the sealed electronics housing extending from the recess.

16. The method of claim 1, wherein attaching the control module to the skull comprises at least one of adhering the control module to the skull using bone cement or fastening the control module to the skull using one or more fasteners.

* * * * *